United States Patent
Block et al.

(10) Patent No.: US 8,927,261 B2
(45) Date of Patent: ***Jan. 6, 2015

(54) METHOD AND DEVICE FOR PURIFYING NUCLEIC ACIDS

(75) Inventors: Dirk Block, Bichl (DE); Ruediger Haenel, Rott (DE); Joerg Kleiber, Penzberg (DE); Manuela Poignee-Heger, Bad Toelz (DE); Thomas Walter, Penzberg (DE); Ralf Zielenski, Lucerne (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/410,161

(22) Filed: Mar. 1, 2012

(65) Prior Publication Data

US 2012/0152818 A1  Jun. 21, 2012

Related U.S. Application Data

(62) Division of application No. 13/006,928, filed on Jan. 14, 2011, now Pat. No. 8,158,349, which is a division of application No. 11/053,065, filed on Feb. 7, 2005, now Pat. No. 7,897,378.

(30) Foreign Application Priority Data

Mar. 18, 2004  (EP) .................................. 04006508
May 28, 2004  (EP) ................................. 040126773

(51) Int. Cl.
| C12M 1/34 | (2006.01) |
| C12M 3/00 | (2006.01) |
| C12Q 1/68 | (2006.01) |
| C12P 19/34 | (2006.01) |
| C12M 1/00 | (2006.01) |
| G01N 15/06 | (2006.01) |
| G01N 33/00 | (2006.01) |
| G01N 33/48 | (2006.01) |
| C07H 21/02 | (2006.01) |
| B01L 3/00 | (2006.01) |
| C12N 15/10 | (2006.01) |

(52) U.S. Cl.
CPC ........... B01L 3/5021 (2013.01); C12N 15/1017 (2013.01); B01L 2300/0609 (2013.01); B01L 2300/0681 (2013.01)
USPC ....... 435/287.2; 435/6.1; 435/6.11; 435/91.1; 435/283.1; 435/287.1; 435/288.6; 422/68.1; 536/23.1

(58) Field of Classification Search
USPC ........ 435/6.1, 6.11, 183, 283.1, 287.1, 287.2, 435/288.6; 436/94, 501; 536/23.1; 422/50, 422/68.1
See application file for complete search history.

(56) References Cited

U.S. PATENT DOCUMENTS 4,270,921 A  6/1981  Graas
4,362,531 A  12/1982  de Steenwinkel et al.
(Continued)

FOREIGN PATENT DOCUMENTS

DE  195 12 361 A1  10/1996
DE  195 12 369 A1  10/1996
(Continued)

OTHER PUBLICATIONS

Stratagene Catalog (1988), p. 39. Published by Stratgene, 11011 North Torrey Pines Road, La Jolla, CA 92037, USA.*

(Continued)

*Primary Examiner* — Frank Lu
(74) *Attorney, Agent, or Firm* — M. Reza Savari

(57) ABSTRACT

The invention concerns a method for isolating and purifying nucleic acids from a sample and a device that is suitable therefore.

16 Claims, 2 Drawing Sheets

(56) References Cited

U.S. PATENT DOCUMENTS

| | | | |
|---|---|---|---|
| 4,500,310 A * | 2/1985 | Christinger | 604/228 |
| 4,729,807 A | 3/1988 | Hede et al. | |
| 4,945,931 A | 8/1990 | Gori | |
| 4,956,298 A | 9/1990 | Diekmann | |
| 5,030,216 A | 7/1991 | Theeuwes et al. | |
| 5,104,533 A | 4/1992 | Szabados | |
| 5,167,477 A | 12/1992 | Falkensson et al. | |
| 5,234,809 A | 8/1993 | Boom et al. | |
| 5,268,464 A | 12/1993 | Brill | |
| 5,378,359 A | 1/1995 | Huse et al. | |
| 5,601,979 A | 2/1997 | Wong | |
| 5,821,436 A | 10/1998 | Bienhaus et al. | |
| 5,910,246 A | 6/1999 | Walter et al. | |
| 6,004,300 A | 12/1999 | Butcher et al. | |
| 6,177,009 B1 | 1/2001 | Sieber et al. | |
| 6,258,531 B1 | 7/2001 | Bienhaus et al. | |
| 6,303,315 B1 | 10/2001 | Skouv | |
| 6,855,816 B1 | 2/2005 | Grimm et al. | |
| 7,897,378 B2 * | 3/2011 | Block et al. | 435/287.2 |
| 8,158,349 B2 * | 4/2012 | Block et al. | 435/6.1 |
| 2002/0086441 A1 * | 7/2002 | Baranov et al. | 436/518 |
| 2004/0157245 A1 | 8/2004 | Radmacher et al. | |
| 2004/0245163 A1 * | 12/2004 | Lim et al. | 210/323.1 |

FOREIGN PATENT DOCUMENTS

| | | |
|---|---|---|
| DE | 298 03 712 U1 | 6/1998 |
| DE | 199 03 507 A1 | 8/2000 |
| DE | 202 18 503 UI | 10/2003 |
| DE | 202004006675.0 | 9/2004 |
| EP | 0 389 063 | 9/1990 |
| EP | 0 588 564 | 3/1994 |
| EP | 0 738 733 | 10/1996 |
| EP | 0 897 978 | 2/1999 |
| EP | 04006508.8 | 8/2004 |
| WO | WO 91/07648 | 5/1991 |
| WO | WO 93/11221 | 6/1993 |
| WO | WO 95/14708 | 6/1995 |
| WO | WO 96/41810 | 12/1996 |
| WO | WO 98/32877 | 7/1998 |
| WO | WO 02/053256 | 7/2002 |
| WO | PCT/EP2005/002722 | 9/2005 |

OTHER PUBLICATIONS

Robbins et al., Vesicular Stomatitis Virus as Model System for Studies of Antisense Oligonucleotide Translation Arrest. Methods in Enzymology, vol. 313, pp. 189-203, 1999.*

Attached Figure 1 with the examiner's handwritings from US Patent No. 6,177,009 B1, Printed on Jan. 7, 2008.

Instruction Manual of Poly(A) Quik.RTM. mRNA isolation kit from Stratagene. Published on 2002.

The definitions of "inlet" and "outlet" from the Free Online Dictionary, Thesaurus and Encyclopedia, Printed on May 5, 2009.

Instruction Manual of Push col. Beta Shield Device and NucTrap. RTM. Probe Purification Column from Stratagene. published on 2001.

Miller, S., et al, 1988, "A simple salting out procedure for extracting DNA from human nucleated cells", Nucleic Acids Research, 16 (3):1215.

Qiagen Plasmid Purification Handbook, Aug. 2003.

Vogelstein, B., et al, 1979, "Preparative and analytical purification of DNA from agarose",Proc. Natl. Acad. Sci. USA, 76 (2):615-619.

The definition of "underpressure" from Wordnik.com Printed on Feb. 3, 2012.

* cited by examiner

METHOD AND DEVICE FOR PURIFYING NUCLEIC ACIDS

CROSS-REFERENCES TO RELATED APPLICATIONS

The present application is a divisional of U.S. application Ser. No. 13/006,928, filed on Jan. 14, 2011, now U.S. Pat. No. 8,158,349, which is a divisional of U.S. application Ser. No. 11/053,065, filed on Feb. 7, 2005, now U.S. Pat. No. 7,897,378, which claims benefit of priority under 35 U.S.C. §119 from EP Application No. 04006508.8, filed Mar. 18, 2004 and EP Application No. 04012677.3 filed May 28, 2004, the contents of which are hereby incorporated by reference in their entireties.

TECHNICAL FIELD

The invention concerns a method for isolating and purifying nucleic acids from a sample and a suitable device therefore.

BACKGROUND OF INVENTION

The introduction of the polymerase chain reaction (PCR) and subsequent alternative amplification systems for nucleic acids has enabled the use of this genetic material as a specimen for diagnostic tests. As a consequence new analytical methods are now available especially for diagnosing hereditary diseases, a predisposition for certain diseases and infectious diseases which, among others, enable an early diagnosis of the condition.

In order to convert the genetic material into a suitable form for enzymatic amplification, it is necessary to release it from the biological sample material. In addition the nucleic acid must be protected from degradation by nucleases from the biological material or the environment and from degradation by chemical reaction conditions. The most stringent requirements concern the freedom from contamination of the biological sample and the nucleic acid isolated therefrom. For the amplification the nucleic acid should be present in a buffered, aqueous, substantially salt-free solution.

Whereas PCR usually uses very small amounts of analyte (pg-ng range), special problems require the processing of a larger quantity of sample. For example, in order to identify circulating tumour cells at a sensitivity of one tumour cell against a background of normal cells, the nucleic acid has to be isolated from 10-20 ml of a blood sample. After homogenizing the sample, an aliquot of the isolated RNA can then be examined for the expression of a tumour-associated gene.

In addition to the classical methods of nucleic acid isolation by means of enzymatic, mechanical or chemical lysis of the sample material, subsequent extraction of the proteins and lipids of phenol and phenol/$CHCl_3$ and precipitation of the nucleic acid from the aqueous phase by ethanol or i-propanol (Sambrook, J., et al., Molecular Cloning, Cold Spring Harbor Laboratory Press, 1989, $2^{nd}$ edition, 9.16-9.23; Ausubel, F. M., et al., Current Protocols in Molecular Biology, John Wiley & Sons, 1987, 2.1.1-2.4.5), several commercial kits have been developed especially for PCR sample preparation in recent years which utilize the property of nucleic acids to bind to glass surfaces under chaotropic salt conditions which has been known since the end of the seventies (Vogelstein, B., et al., Proc. Natl. Acad. Sci. USA 75 (1979) 615-619). Other constituents of biological material such as proteins, lipids or salts, are not bound and are therefore separated. Centrifugation vessels with glass fleece inlays or silica gel suspensions which allow a batch process are known. In addition multiple devices are known in a strip and 96-well microtitre plate format with the glass fleeces recessed into the base which can be operated with the aid of a vacuum chamber attached underneath as well as by, centrifugation. In these methods the volume of the samples is often limited. Moreover, large amounts of buffer are necessary to effectively elute the nucleic acids from the glass fleeces which results in a diluted solution of the isolated molecules and requires additional preparation steps for certain applications.

A modified method (Miller et al., Nucl. Acids Res. (1988) 16: 1215) uses a concentrated salt solution to precipitate proteins and other accompanying substances after lysis of the sample material. The nucleic acids in the supernatant are then precipitated by ethanol and collected by centrifugation. After the nucleic acids have been dissolved they can be used for amplification.

WO 93/11221 discloses a method and a device for isolating and purifying nucleic acids which uses anion exchangers and mineral carrier substances. U.S. Pat. No. 5,104,533 discloses a filtration unit with pressure compensation. U.S. Pat. No. 4,270,921 discloses the combination of a microcolumn and a centrifuge tube. WO 98/32877 discloses a device for isolating nucleic acids which is composed of two vessels connected by a closure element which contains a material for binding nucleic acids. U.S. Pat. No. 4,956,298 discloses a separation or reaction column consisting of a centrifuging vessel and a receiving body where the receiving body contains a column material and the centrifuging vessel collects the effluent of the receiving body. DE 19512361 discloses a method for isolating a biological material which uses a compressible porous matrix to bind the biological material and compresses the material in order to elute the material. EP 588564 describes a device for affinity separation comprising a capture membrane located in a pipette tip. WO 96/41810 discloses the removal of DNA from a cell suspension with the aid of a hollow membrane filter and an ion exchange step. The manufacture of a device containing a material for binding nucleic acids is known from EP 738733. WO 02/053256 discloses a device and a method for purification comprising a sample holder with a column insert portion, whereas a column module is secured in said column insert portion. U.S. Pat. No. 6,177,009 and the German utility models DE 298 03 712 U1 and DE 202 18 503 U1 describe a device for treating biomolecules comprising a separation column which has a separation device and a collecting vessel for the liquid that flows out.

SUMMARY OF THE INVENTION

The object of the present invention was to provide a new device and a new method for purifying or isolating nucleic acids from larger sample volumes.

The object is achieved according to the invention by a device whose individual components are shown in FIG. 1. Furthermore a method is described in which the device according to the invention is used and whose individual phases are also shown schematically and as an example in FIG. 1. The method according to the invention in which the device according to the invention is used ensures a larger yield of nucleic acids.

One subject matter of the present invention is a device for purifying or isolating nucleic acids consisting of a first hollow body 100 with an inlet opening 101 for a sample and an outlet opening 102 and a second hollow body 200 with an inlet opening 201 and an outlet opening 202, wherein the inlet opening of the second hollow body 201 is functionally connected to the outlet opening of the first hollow body 102, the first and the second hollow body can be detached from one another, a nucleic acid-binding material 203 is located in front of the outlet opening of the second hollow body 202, the second hollow body 200 has a smaller volume compared to the first hollow body 100 and the first hollow body 100 has a volume of more than 5 ml.

Another aspect of the invention concerns a closable vessel 400 which contains a device according to the invention.

The invention also concerns a method for purifying or isolating nucleic acids from a sample comprising the steps:
a) providing the device according to the invention,
b) transferring the sample into the device through the inlet opening in the first hollow body,
c) passage of the sample from the second hollow body through the nucleic acid-binding material into a vessel during which the nucleic acids bind to the nucleic acid-binding material,
d) optionally washing the nucleic acids bound to the nucleic acid-binding material,
e) detaching the second hollow body from the first hollow body and transferring the second hollow body into a receiving vessel 900,
f) washing the nucleic acids bound to the nucleic acid-binding material,
g) eluting the nucleic acids bound to the nucleic acid-binding material whereby the nucleic acids are collected in a second receiving vessel 13 and are thus purified or isolated.

The invention also concerns a kit for purifying or isolating nucleic acids from a sample composed of a device according to the invention or a vessel according to the invention and chaotropic reagents for binding the nucleic acids to the nucleic acid-binding material.

Another subject matter of the invention is the use of a device according to the invention or of a vessel according to the invention to purify or isolate nucleic acids from a sample.

A nucleic acid-binding material is understood as a material to which nucleic acids bind non-covalently under certain conditions whereas other substances in a sample do not bind under these conditions. This nucleic acid binding is reversible and hence the nucleic acids can be subsequently eluted again from the material by changing the conditions.

A matrix is understood within the scope of this invention as a material in which particles or fibres of the nucleic acid-binding material are embedded. This matrix material is permeable to liquids so that the sample can pass through the matrix, the nucleic acids can make contact with the nucleic acid-binding material and other components of the sample can leave the matrix. Solid materials having a small diameter are referred to as particles by a person skilled in the art. These particles preferably have an essentially spherical surface. Lamellar and filamentary particles made of nucleic acid-binding material are referred to as fibres.

Within the scope of this invention a hollow body is a hollow structure with an inlet opening through which a sample can enter the hollow body and an outlet opening through which the sample can again leave the hollow body. In contrast a vessel is a hollow structure with only one inlet opening through which a sample can enter the vessel. Hence it can be used to collect a sample.

Within the scope of this invention a functional connection of hollow bodies is understood to mean that the two hollow bodies are connected in such a manner that it is possible to carry out the method according to the present invention. For this purpose it should be possible to detach the connection as required, it should be impermeable to liquids and, for certain applications, it should also prevent air exchange with the environment. Furthermore it should ensure a passage of the sample from the first hollow body into the second hollow body without loss.

Chaotropic reagents are understood as substances which change the secondary, tertiary and/or quarternary structure of proteins or nucleic acids but do not affect at least their primary structure. Examples are guanidinium thiocyanate, guanidinium hydrochloride, NaI, KI, sodium thiocyanate or combinations of these substances. Within the scope of this invention chaotropic reagents are understood as all chemical substances which disturb the ordered structure of liquid water and thus cause DNA or RNA to bind from this aqueous solution to a glass surface. Other substances such as NaCl, KCl or CaCl2 may be present in the solution in order to modify the ionic strength. The property of DNA and RNA to bind under chaotropic conditions to glass surfaces can be utilized to isolate them from a solution containing other biological materials since the binding to the glass surface is reversible. If, for example, the concentration of the chaotropic reagents is reduced or the chaotropic reagents are entirely removed, the DNA or RNA can be eluted again.

DETAILED DESCRIPTION OF THE INVENTION

Figure 1:
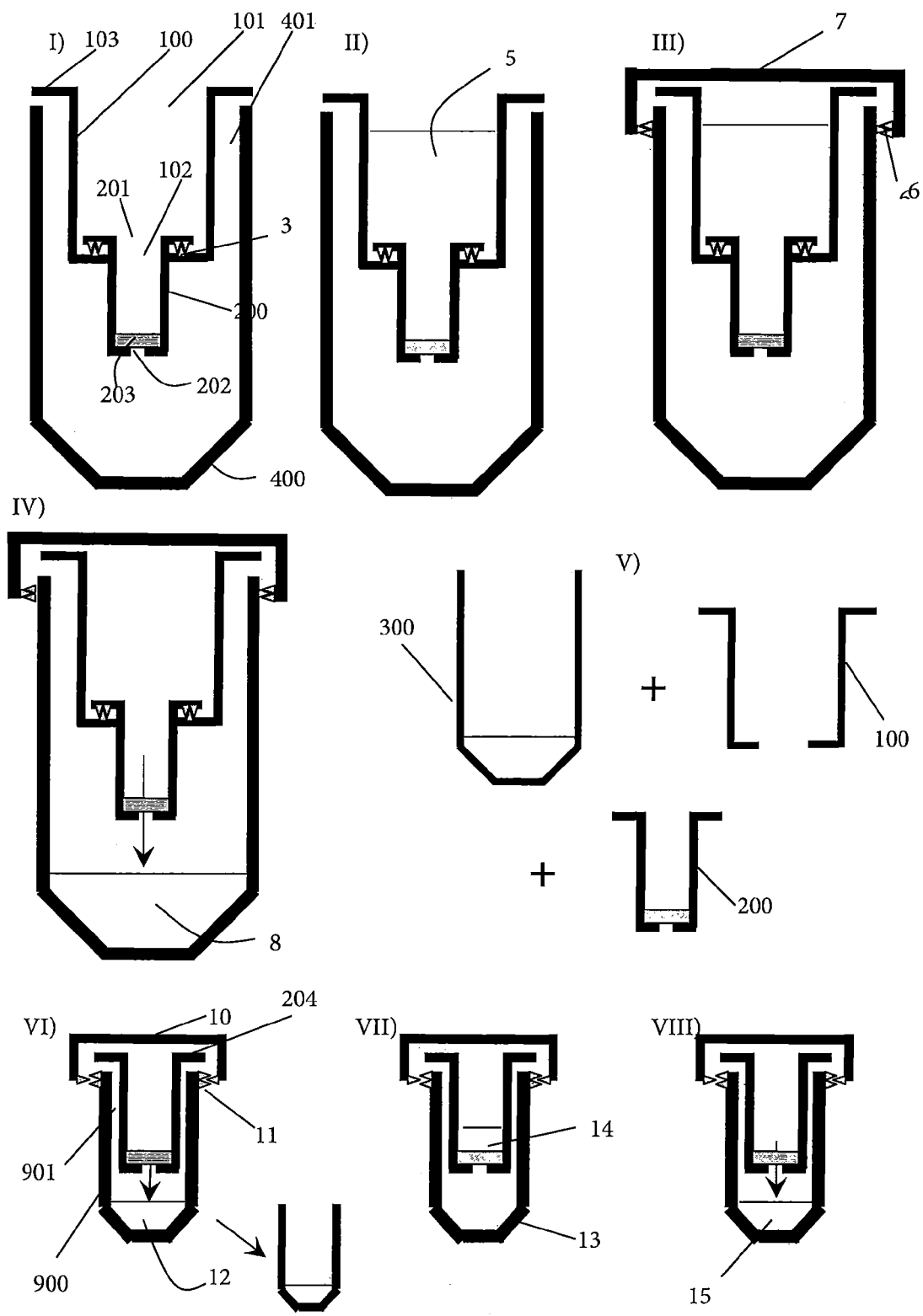
FIG. 1: Schematic representation of the method according to the invention shown as an example using the device according to the invention.

One subject matter of the present invention is a device for purifying or isolating nucleic acids consisting of a first hollow body 100 with an inlet opening 101 for a sample and an outlet opening 102 and a second hollow body 200 with an inlet opening 201 and an outlet opening 202, wherein the inlet opening of the second hollow body 201 is functionally connected to the outlet opening of the first hollow body 102, the first and the second hollow body can be detached from one another, a nucleic acid-binding material 203 is located in front of the outlet opening of the second hollow body 202, the second hollow body 200 has a smaller volume compared to the first hollow body 100 and the first hollow body 100 has a volume of more than 5 ml.

Materials that bind nucleic acids are known to a person skilled in the art. The material can be particulate as well as fibrous. If the material is composed of particles it has proven to be advantageous to immobilize these particles for example by incorporating them between liquid-permeable lamellae e.g. fabrics or fleeces made of a fibrous material such as cellulose or plastics which have such narrow pores that the particles are held between the lamellae. The nucleic acid-binding material is preferably mainly composed of silicon dioxide or contains silicon dioxide in the form of fibres or particles. The nucleic acid-binding material is particularly preferably a glass fleece or a silica gel or it is composed of zeolite. The nucleic acid-binding material is also preferably composed of metal oxides or mixed metal oxides in the form of fibres or particles. The nucleic acid-binding material is particularly preferably composed of aluminium oxide, hafnium oxide or zirconium oxide or contains aluminium oxide, hafnium oxide or zirconium oxide in the form of fibres or particles.

The nucleic acid-binding material is preferably a fibrous material e.g. in the form of fabrics or fleeces. Suitable materials are for example known from methods for isolating nucleic acids with the aid of centrifugation tubes (EP 738733) or multiple devices in a strip format (EP 616638). The nucleic acid-binding material must have the property that the sample liquid can pass through the material without any additional action of force or by applying force e.g. by applying pressure or underpressure. However, since the nucleic acids are not bound in the present method by filtration of the nucleic acids from the sample but by a method which utilizes the affinity of nucleic acids to surfaces, it is possible to use a relatively coarsely porous material. This facilitates the flow even of relatively viscous sample liquids.

The liquid-permeable, nucleic acid-binding material is able to bind nucleic acids but allows passage of the surrounding liquid and other components dissolved therein such as proteins etc. In a first variant the nucleic acids can be bound sequence-specifically by capture probes attached to the surface of the material. The capture probes have a base sequence which can bind to a complementary base sequence in the nucleic acids to be isolated under hybridizing conditions. The use of sequence-specific materials allows the selective isolation of nucleic acids of a particular sequence. A method for binding nucleic acids to peptidic nucleic acids on the surface of solids is described for example in WO 95/14708.

Zirconium oxide, hafnium oxide or aluminium oxide (EP 897978) and also titanium oxide are for example suitable as the nucleic acid-binding material. The hydrated surfaces of these materials have sufficient positive charges to bind negatively charged nucleic acids. The surface of the oxides can be hydrated in basic solutions. The nucleic acids can then be subsequently eluted by washing with low-molecular alcohols or other wash solutions having a low pH.

In a preferred embodiment the liquid-permeable, nucleic acid-binding material has a surface containing glass. The property of glass to bind nucleic acids in a particulate and fibrous form has been known for a long time. Chaotropic reagents such as guanidinium thiocyanate, guanidinium hydrochloride, NaI, KI, sodium thiocyanate or combinations of these substances are necessary for the reversible binding to glass surfaces (U.S. Pat. No. 5,234,809).

DE-A-19512369 describes the use of glass fleeces to isolate nucleic acids. A method is proposed in EP-B-0389 063 in which the sample is mixed with a mixture of a chaotropic guanidinium salt and silica particles. Under these conditions nucleic acids bind sequence-independently to the silica surface. The other sample components can be washed away and the nucleic acids can be subsequently eluted in an aqueous buffer.

Nucleic acids within the sense of the invention are understood as nucleic acids of any origin e.g. nucleic acids of viroid, viral, bacterial or cellular origin. If the nucleic acids are not readily accessible in the sample, they are preferably made accessible with appropriate reagents. This includes changing the pH (alkaline), heat, repeated extreme changes in temperature (freezing/thawing), changing the physiological growth conditions (osmotic pressure), action of detergents, chaotropic salts or enzymes (e.g. proteases and lipases). Sample materials from which nucleic acids can be released in this manner are in particular cell-containing media, cell smears and tissue sections. The nucleic acids can be RNA as well as DNA.

The device according to the invention consists of two hollow bodies 100/200 which are connected by a functional connection 3 and each of which has an inlet opening 101/201 and an outlet opening 102/202 for a sample. This device according to the invention is preferably shaped such that it at least partially fits into a vessel 400. In this context functionally connected means that the two hollow bodies are connected in such a manner that it is possible to carry out the method according to the present invention. For this purpose it should be possible to detach the connection as required, it should be impermeable to liquids and, for certain applications, it should also prevent air exchange with the environment. Furthermore it should ensure a passage of the sample from the first hollow body into the second hollow body without loss. These hollow bodies are preferably essentially cylinders. The openings are preferably essentially round. In addition to a cylindrical portion at the inlet opening, the first hollow body particularly preferably also has a section that narrows conically towards its outlet opening. The first hollow body preferably has a volume of more than 5 ml. Once the sample 5 has passed through the outlet opening 102 of the hollow body 100, it enters the second hollow body 200 without loss through the preferably round inlet opening 201 by means of the functional connection 3.

The liquid permeable, nucleic acid-binding material 203 is located in the second hollow body. The nucleic acid-binding material is disposed at the preferably round outlet opening 202 of the hollow body in such a manner that the emerging sample liquid 5 has to pass through the nucleic acid-binding material. In this process the nucleic acids are bound to the nucleic acid-binding material.

The second hollow body can be similar to the first hollow body with regard to its design as well as material. In particular the hollow bodies should be able to receive at least the volume of the sample liquid 5. The second hollow body preferably has a smaller volume compared to the first hollow body. This hollow body is preferably shaped such that it at least partially fits into a receiving vessel 900. In addition the second hollow body consists of a material and has a size so that it is suitable for centrifugation at high speeds of up to 14,000 revolutions per minute.

Both hollow bodies have means that enable them to be functionally and reversibly connected together. The functional connection 3 of the first and second hollow body is preferably a screw connection i.e. for example an outer or inner screw thread. If the first hollow body for example has a thread, the means of the second hollow body is a matching counter thread. In another preferred embodiment of the present invention the first and the second hollow body are connected together by pressing forces e.g. by means of a plug connection.

The two hollow bodies preferably together have a volume which allows them to receive the entire sample and other reagents e.g. to facilitate the binding of nucleic acids to the nucleic acid-binding material. The volume is more than 500 microliters, preferably between 1 and 1000 ml, particularly preferably between 1 and 100 ml and most preferably between 5 and 50 ml or 10 and 30 ml. A volume of 10, 20 or 30 ml is particularly preferred. The first hollow body has a preferred volume between 1 and 100 ml, particularly preferred between 5 and 50 ml, most preferred between 10 and 30 ml. The second hollow body has preferably a volume of below 2 ml, particularly preferred between 1 and 2 ml.

A preferred variant of the device according to the present invention is a device characterized in that the two hollow bodies together have a volume of between 5 and 50 ml.

Furthermore the first hollow body preferably has means near to its inlet opening 101 for holding 103 the hollow body in a vessel 400 such that its position is fixed. This vessel has an inlet opening 401 which is preferably round. The vessel preferably has a cylindrical portion at the inlet opening 401 and a conical region at its end. The vessel is used to receive the liquid 8 which emerges from the second hollow body 200 after it has passed through the nucleic acid-binding material 203. The vessel can preferably be closed.

The vessel 400 is particularly preferably shaped and provided with closure means 6 in such a manner that it can completely receive both functionally connected hollow bodies 100/200 and the vessel 400 can be closed with a closure element 7. The closure element is preferably a screw cap made of plastic. A circular flange is preferred as the means for holding 103 the first hollow body in the vessel 400 which protrudes beyond the edge of the vessel such that the hollow body rests on it and cannot penetrate further into the vessel. This circular flange is preferably shaped such that it is clamped with the vessel by the closure element 7 and thus acts as a seal. In this case the closure element is preferably a screw cap that is placed from above and the vessel then has the corresponding counter thread.

Alternatively the vessel can have a section that narrows conically at its inlet opening 401 such that the first hollow body cannot penetrate further into the vessel at a defined position even without additional means for holding it. In this case the vessel can also be closed with a closure element. It is also conceivable that the two functionally connected hollow bodies only partially fit into the vessel in which case at least the outlet opening of the second hollow body must completely extend into the vessel.

Figure 2:
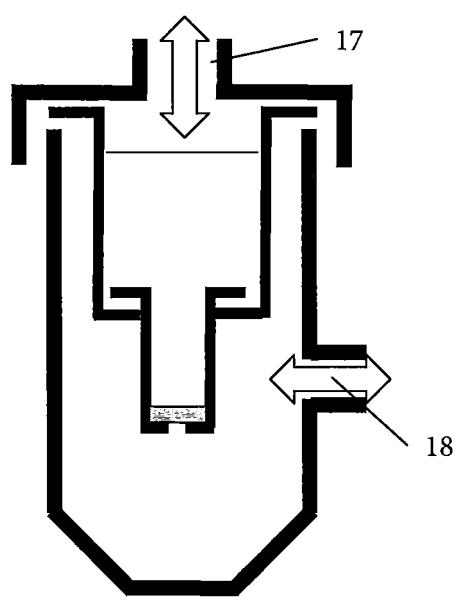
FIG. 2: Alternative embodiment of the device according to the invention in which means are provided that enable a pressure difference to be generated and thus ensure passage of the sample through the nucleic acid-binding material.

In a further preferred variant of the device according to the invention which is shown in FIG. 2, the vessel 400 is provided with means for applying a pressure difference. This pressure difference can execute or support the passage of the sample through the nucleic acid-binding material. For this purpose the vessel is provided with a connecting piece 16 for applying overpressure or underpressure and the closure element 7 is provided with a pressure-equalizing connection 17. In this variant of the device it is necessary that the site connecting the two hollow bodies is also impermeable to gases since otherwise a pressure difference cannot build up across the nucleic acid-binding material.

The second hollow body 200 is preferably shaped such that it at least partially fits into a receiving vessel 900. This receiving vessel preferably has an essentially round inlet opening 901. The receiving vessel 900 is preferably closable and consists of a cylindrical portion at the inlet opening and a conical portion at its end. The receiving vessel is particularly preferably designed such that the second hollow body 200 provided with holding means 204 fits into it and that the vessel can be closed with a closure element 10. Like the first hollow body 100, the second hollow body also preferably has a circular flange as the holding means 204 which extends over the edge of the receiving vessel. When using a screw cap 10 with a thread 11 the circular flange is clamped with the receiving vessel and acts as a seal. Also in this case the receiving vessel may also have a conical shape in order to hold the second hollow body at a defined position in which the hollow body completely or partially penetrates into the receiving vessel.

In a further variant of the present invention the receiving vessel is preferably provided with means for applying a pressure difference. This pressure difference can execute or support the removal of residual liquid from the fleece and the elution of the nucleic acids from the material. For this purpose the receiving vessel is provided with a connecting piece for applying an overpressure or underpressure and the closure element is provided with a pressure-equalizing connection.

The first or the second hollow body, the vessel or the receiving vessel of the device according to the invention are made of materials that do not bind nucleic acids. The first or the second hollow body, the vessel or the receiving vessel of the device according to the invention are preferably made of plastic, metal or composite material. Plastics such as polypropylene, polystyrene, polyethylene or Luran® are particularly preferred. These have the advantage that they can be easily manufactured in a multiple injection process and having a high mechanical stability under the conditions of the isolation method according to the invention.

Plastics that can be injection moulded are particularly preferred as materials for the hollow body because they already allow the introduction of the nucleic acid-binding, liquid-permeable material during the manufacture of the second hollow body. Especially in the case of glass fibre fleeces the material can already be permanently poured into the closure element already during the injection moulding process. However, it is also possible to only attach the material after the manufacture of the second hollow body in the injection moulding process e.g. by gluing, welding or by fixation with a clamp ring. Processes for manufacturing a hollow body containing nucleic acid-binding material are described in the patent document EP 0 738 733. Such separation columns containing nucleic acid-binding material are also commercially available (High Pure™ column from Roche Diagnostics GmbH, Mannheim).

The invention also concerns a closable vessel which contains a device according to the invention. The closable vessel is preferable shaped such that it is able to receive the entire inventive connection of the two hollow bodies and can be closed by means of a closure element. The closable vessel is particularly preferably a commercial centrifugation vessel such as a plastic tube (Falcon tube) which has a filling volume of 50 ml and can be closed by means of a screw cap.

Another aspect of the present invention is a method for purifying or isolating nucleic acids from a sample comprising the steps:

a) providing the device according to the invention,
b) transferring the sample into the device through the inlet opening in the first hollow body,
c) passage of the sample from the second hollow body through the nucleic acid-binding material into a vessel during which the nucleic acids bind to the nucleic acid-binding material,
d) optionally washing the nucleic acids bound to the nucleic acid-binding material,
e) detaching the second hollow body from the first hollow body and transferring the second hollow body into a receiving vessel 900,
f) washing the nucleic acids bound to the nucleic acid-binding material,
g) eluting the nucleic acids bound to the nucleic acid-binding material whereby the nucleic acids are collected in a second receiving vessel 13 and are thus purified or isolated.

A preferred variant of the method of the present invention uses a device according to the invention with a nucleic acid-binding material which is mainly composed of silicon dioxide or contains silicon dioxide in the form of particles or fibres or is particularly preferably a glass fleece or silica gel or consists of zeolite and a sample to which chaotropic reagents are already added through the inlet opening of the first hollow body before transfer into the device such that the concentration of the chaotropic reagents is between 1 M and 8 M.

A preferred embodiment of the method according to the invention that is based on the device according to the invention is described in the following. Firstly the cells of 5 to 30 ml whole blood, serum, plasma or other body fluids are lysed, disrupted and the reagents that are additionally required e.g. a chaotropic salt or/and protease are added to the sample liquid. In addition the device according to the invention is placed in a vessel for collecting the nucleic acid-free liquid (see step I and II in FIG. 1). After the sample 5 has been transferred into the device through the inlet opening of the first hollow body, the vessel is preferably tightly closed with a cap (step III in FIG. 1.

In the next step the sample liquid is passed through the nucleic acid-binding material (step IV in FIG. 1). The sample can be passed through either already by means of gravitational force or also preferably by centrifuging the device. The sample can also be preferably passed through the nucleic acid-binding material by applying a pressure difference. In this embodiment of the invention (see FIG. 2) the device is additionally provided with means e.g. two connecting pieces 16/17 for applying the pressure. One connecting piece for applying the overpressure or underpressure is preferably located on the vessel itself and the second connecting piece is located on the closure element of the vessel to serve as a pressure-equalizing connection.

During passage of the sample liquid through the nucleic acid-binding material, the nucleic acids present in the sample are bound to the nucleic acid-binding material while other sample components together with the liquid 8 pass into the vessel. The isolated nucleic acids are now in the nucleic acid-binding material of the second hollow body which, if required, can be separated from the first hollow body and processed further in any desired manner.

Since certain quantities of liquids containing contaminants still usually adhere to the liquid-permeable material even after centrifugation, it is possible to remove substances that are still adhering by an optional washing step in order to isolate particularly pure nucleic acids before the device is removed from the vessel and the functional connection of the hollow bodies is separated. For this purpose the washing fluid can for example be added through the inlet opening of the first hollow body so that it rinses the material to which the nucleic acids are bound while it passes through and is then collected in the vessel. The washing step can preferably be carried out applying a pressure difference or by centrifuging the device.

In order to detach the nucleic acids again from the liquid-permeable, nucleic acid-binding material, the second hollow body can be removed from the device (step V in FIG. 1). For this purpose the second hollow body is preferably connected to a receiving vessel 900 after it has been separated from the first hollow body in order to firstly remove residual liquid 12 present in the fleece (step VI in FIG. 1). This washing is preferably carried out by centrifuging the device since the second hollow body connected to the receiving vessel can be subjected to very high centrifugal forces due to its small dimensions. Subsequently the second hollow body is connected to a second receiving vessel 13 which should collect the eluate (step VII in FIG. 1). The elution liquid 14 is composed such that it abolishes the binding of the nucleic acids to the nucleic acid-binding material. The conditions under which the nucleic acids can be detached again depend on the material that is used and the process can again be supported by applying a pressure difference or by centrifugation (step VIII in FIG. 1).

The elution is preferably carried out by centrifuging since this enables the nucleic acids to be dissolved in very small volumes of elution liquid and also allows a reduction in the amount of nucleic acids remaining in the nucleic acid-binding material. The centrifugation for the elution and washing is preferably carried out using larger centrifugal forces than the centrifugation for the passage of the sample and the optional washing. The centrifugation for elution and washing is preferably carried out at more than 5000 g and the centrifugation for sample passage and optionally washing is preferably carried out at less than 5000 g. The second hollow body and the receiving vessel are particularly preferably shaped such that they can be centrifuged together e.g. in an Eppendorf centrifuge (Eppendorf, Hamburg, Germany) at more than 10,000 g. This is possible since the receiving vessel only has to have a considerably smaller volume than the first vessel which can only be subjected to a considerably lower centrifugal force (e.g. in a Beckman bench centrifuge (Beckman Coulter, Inc., USA) at about 3000 g) and would thus require more elution liquid. Hence the device according to the invention is not only suitable for isolating nucleic acids but also for transferring nucleic acids from a larger 5 into a smaller volume 15.

The volume of the device for purifying or isolating nucleic acids is an important feature for the present invention. On the one hand, the volume of the device must be large in order to apply diluted, voluminous samples and on the other hand, the size of the device must be small in order to realize a lysis procedure with small amounts of lysis buffer. The necessary amount of lysis buffer for the efficient elution of the nucleic acid is, among others, depending on the size of the nucleic acid-binding material and on the supporting force of the lysis procedure. The reversible coupling of a large first hollow body with a small second hollow body comprising the nucleic acid-binding material solves both said requirements. First, the overall volume of both hollow bodies provides the applicability of diluted, voluminous samples during the binding process. Second, after the binding process the small second hollow body can be removed from the device and the nucleic acid may be eluted with a much higher centrifugation force as possible with a state of the art device applicable for the same initial sample volume.

Another aspect of the invention is a kit for purifying or isolating nucleic acids from a sample which is composed of a device according to the invention or a vessel according to the invention and chaotropic reagents for binding the nucleic acids to the nucleic acid-binding material. The kit can additionally contain other plastic parts that are required to carry out the method according to the invention such as microtitre plates or simple reaction vessels such as Eppendorf reaction vessels (Eppendorf, Hamburg, Germany). In addition the kit can contain further reagents that are necessary for the method according to the invention e.g. lysis buffer containing chaotropic reagents, detergent, alcohol or mixtures of these substances that lyse cells, washing buffer containing chaotropic reagents and/or alcohol or buffer with acidic pH to wash the nucleic acid-binding material to which the nucleic acids are bound or elution buffer which enables the nucleic acids to be detached from the nucleic acid-binding material. According to the invention these components of the kit can be provided individually or in storage containers. The reagents are usually offered ready-to-use but can also be sold in the form of stock solutions that have to be diluted before use.

The invention also concerns the use of a device according to the invention or a vessel according to the invention to purify or isolate nucleic acids from a sample.

Specifically the invention encompasses the following aspects:

1. Device for purifying or isolating nucleic acids consisting of a first hollow body 100 with an inlet opening 101 for a sample and an outlet opening 102 and a second hollow body 200 with an inlet opening 201 and an outlet opening 202 wherein the inlet opening of the second hollow body 201 is functionally connected to the outlet opening of the first hollow body 102, the first and the second hollow body can be detached from one another and a nucleic acid-binding material 203 is located in front of the outlet opening of the second hollow body 202.

2. Device according to item 1, wherein the second hollow body has a smaller volume compared to the first hollow body.
3. Device according to one of the items 1 or 2, wherein the device is shaped such that it at least partially fits into a vessel 400.
4. Device according to one of the items 1 to 3, wherein the second hollow body is shaped such that it at least partially fits into a receiving vessel 900.
5. Device according to one of the items 1 to 4, wherein the first and the second hollow body are connected together by a screwed joint.
6. Device according to one of the items 1 to 4, wherein the first and the second hollow body are connected together by pressing forces.
7. Device according to one of the items 1 to 6, wherein the first and/or the second hollow body are essentially cylinders.
8. Device according to item 7, wherein the first hollow body in addition to its cylindrical section at the inlet opening, has a section that becomes conically narrower towards its outlet opening.
9. Device according to one of the items 1 to 8, wherein the openings of the first and/or of the second hollow body are essentially round.
10. Device according to one of the items 1 to 9, characterized in that the first hollow body has a volume of more than 5 ml.
11. Device according to one of the items 3 to 10, wherein the vessel is closable.
12. Device according to one of the items 3 to 11, wherein the vessel consists of a cylindrical section at the inlet opening and a conical section at its end.
13. Device according to one of the items 3 to 12, wherein the vessel has means for applying a pressure difference.
14. Device according to one of the items 4 to 13, wherein the receiving vessel is closable.
15. Device according to one of the items 4 to 14, wherein the receiving vessel is closable and consists of a cylindrical section at the inlet opening 401 and a conical section at its end.
16. Device according to one of the items 4 to 15, wherein the receiving vessel has means for applying a pressure difference.
17. Device according to one of the items 4 to 16, wherein the inlet openings of the vessel 401 and/or of the receiving vessel 901 are essentially round.
18. Device according to one of the items 1 to 17, characterized in that the nucleic acid-binding material is mainly composed of silicon dioxide or contains silicon dioxide in the form of fibres or particles.
19. Device according to one of the items 1 to 18, characterized in that the nucleic acid-binding material is a glass fleece or a silica gel or is composed of zeolite.
20. Device according to one of the items 1 to 19, characterized in that the nucleic acid-binding material is composed of metal oxides or mixed metal oxides or contains metal oxides or mixed metal oxides in the form of fibres or particles.
21. Device according to one of the items 1 to 20, characterized in that the nucleic acid-binding material is composed of aluminium oxide, hafnium oxide or zirconium oxide or aluminium oxide, hafnium oxide or zirconium oxide in the form of fibres or particles.
22. Device according to one of the items 1 to 21, characterized in that the first or the second hollow body, the vessel or the receiving vessel are made of a material that does not bind nucleic acids.
23. Device according to one of the items 1 to 22, characterized in that the first or the second hollow body, the vessel or the receiving vessel is composed of plastic, metal or a composite material.
24. Device according to item 23, characterized in that the second hollow body is made of polypropylene.
25. Closable vessel 400 which contains a device according to one of the items 1 to 24.
26. Method for purifying or isolating nucleic acids from a sample by
    a) providing a device according to one of the items 1 to 25,
    b) transferring the sample into the device through the inlet opening in the first hollow body,
    c) passage of the sample from the second hollow body through the nucleic acid-binding material into a vessel during which the nucleic acids bind to the nucleic acid-binding material,
    d) optionally washing the nucleic acids bound to the nucleic acid-binding material,
    e) detaching the second hollow body from the first hollow body and transferring the second hollow body into a receiving vessel 900,
    f) washing the nucleic acids bound to the nucleic acid-binding material
    g) eluting the nucleic acids bound to the nucleic acid-binding material whereby the nucleic acids are collected in a second receiving vessel 13 and are thus purified or isolated.
27. Method according to item 26, characterized in that a device as claimed in one of the items 18 or 19 is used and that chaotropic reagents are additionally added to the sample through the inlet opening in the first hollow body before transfer into the device such that the concentration of the chaotropic reagents is between 1 M and 8 M.
28. Method according to item 26, characterized in that the passage of the sample in step c), the optional washing in step d), the washing in step f) or the elution in step g) is carried out by applying a pressure difference.
29. Method according to item 26, characterized in that the passage of the sample in step c), the optional washing in step d), the washing in step f) or the elution in step g) is carried out by centrifugation.
30. Method according to item 29, characterized in that the centrifugation in steps f) and g) is carried out at a larger centrifugal force compared to the centrifugation in steps c) and d).
31. Method according to item 29, characterized in that the centrifugation in steps c) and d) is carried out with a centrifugal force of less than 5000 g.
32. Method according to item 29, characterized in that the centrifugation in steps f) and g) is carried out with a centrifugal force of more than 5000 g.
33. Kit for purifying or isolating nucleic acids from a sample composed of
    a) a device according to one of the items 1 to 24 or a vessel according to item 25,
    b) chaotropic reagents for binding the nucleic acids to the nucleic acid-binding material.
34. Use of a device according to one of the items 1 to 24 or a vessel according to item 25 to purify or isolate nucleic acids from a sample.

The invention is further elucidated by the following examples, publications and figures the protective scope of which is derived from the patent claims. The described methods are to be understood as examples which still describe the invention even after modifications.

EXAMPLES

Example 1

The following example of a DNA isolation from 5 ml serum is intended to further elucidate the present invention. The so-called "UpScale HighPure" method utilizes the so-called "UpScale HighPure" kit which is composed of a commercially available "HighPure™ Column" (Roche Diagnostics GmbH, Mannheim, Germany), a pluggable volume attachment and reagents that are identical to the reagents of the "MagNA Pure® LC Total Nucleic Acid Isolation Kit-Large Volume" (Roche Diagnostics GmbH, Mannheim, Germany). The volume attachment (made of polypropylene) has a cylindrical shape in this example (inner diameter 2.5 cm, length 5 cm) with a filling volume of about 25 ml, a round inlet opening and an outlet opening in which a HighPure column (volume about 1.5 ml) can be attached. An Eppendorf centrifuge (Eppendorf, Hamburg, Germany), a Beckman centrifuge (Beckman Coulter, Inc., USA) with 50 ml Falcon tubes, a commercial vortexer and Eppendorf reaction vessels (Eppendorf, Hamburg, Germany) are also used for the DNA isolation by means of the "UpScale HighPure" method.

Procedure for the DNA Isolation

250 µl of a 40 mg/ml proteinase K solution are placed in a 50 ml Falcon tube. 5 ml sample (serum or plasma) is added, vortexed and then incubated for 10 min at room temperature. In the next step, 6.25 ml lysis/binding buffer are added, vortexed and the solution is incubated for 10 min at 65° C. This is followed by a centrifugation at 1900 g (removal of foam). In the next step 3.125 ml isopropanol are added, mixed and centrifuged for 1 min at 1900 g, then the mixture is allowed to stand for 10 min at room temperature. In the next step the mixture is applied in one portion (ca. 15 ml) to the volume attachment of the device, the remaining residual liquid is also applied to the column by pipetting. It is firstly centrifuged for 2 min at 1900 g (including acceleration), subsequently for 1 min at 3300 g. In the next step the eluate is discarded.

This is followed by various washing steps (the used washing buffers are commercially available "MagNA Pure® LC Total Nucleic Acid Isolation Kit-Large Volume", cat. No. 3264793, Roche Diagnostics GmbH, Mannheim, Germany): Firstly the device is placed in a new 50 ml Falcon tube, 2 ml washing buffer 1 is added and centrifuged for 2 min at 3300 g. Afterwards 2 ml washing buffer 2 is added and centrifuged for 2 min at 3300 g. In the next washing step 2 ml washing buffer 3 is added and centrifuged for 2 min at 3300 g (the 3 washing steps can be carried out without changing the Falcon tube). The volume attachment is now removed from the High Pure column and the High Pure column is placed in an Eppendorf cup, closed with a cap and centrifuged in an Eppendorf centrifuge for 1 min at 20,000 g. This removes residual liquid from the fleece.

The next step comprises eluting the DNA. 50-100 µl elution buffer is applied to the fleece and the High Pure column is closed with a cap. Afterwards it is incubated for 3 min at room temperature and subsequently centrifuged for 1 min at 20,000 g in the Eppendorf centrifuge. The Eppendorf reaction vessel contains the eluate and the HighPure™ column can be discarded.

Example 2

The following example shows a comparison of a DNA isolation according to the inventive method and an isolation according to the state of the art. A serum sample is prepared analogously to example 1 and evenly divided between 2 HighPure™ columns with a volume attachment. The experimental procedure for both columns is identical up to the step of removing residual liquid. In one of the columns the volume attachment is separated from the HighPure column in the following, the residual liquid in the fleece is removed by centrifugation with the aid of an Eppendorf centrifuge (about 15 µl) and the bound nucleic acid is subsequently eluted in 50 µl with the aid of the Eppendorf centrifuge.

In contrast in the second column the connection between the HighPure column and the volume attachment is retained, the entire device is inserted in a Falcon tube and the elution is carried out with 50 µl solution in a Beckman centrifuge (2 min 3300 g), without previously removing the residual liquid from the fleece.

Results show that on average the DNA yield was about 30% lower over 10 experiments without separating the device and without the Eppendorf centrifuge.

Example 3

The following example shows an other comparison of a DNA isolation according to the inventive method and an isolation according to the state of the art. A serum sample is prepared analogously to example 1 and evenly divided between a HighPure™ column with volume attachment and a "NucleoSpin® Funnel" column from Macherey & Nagel, Düren, Germany (Cat.-No. 740959). The experimental procedure for both columns is identical up to the step of removing residual liquid. In case of the HighPure™ column the volume attachment is separated from the HighPure column in the following, the residual liquid in the fleece is removed by centrifugation with the aid of an Eppendorf centrifuge (about 15 µl) and the bound nucleic acid is subsequently eluted in 60 µl with the aid of the Eppendorf centrifuge.

In contrast the column of Macherey & Nagel is inserted in a Falcon tube and the elution is carried out with 60 µl solution in a Beckman centrifuge (2 min 3300 g), without previously removing the residual liquid from the fleece.

Results show that on average the DNA yield using a HighPure™ column with volume attachment was about a factor of 3 to 4 better over 5 different serum probes (3 determinations per probe) than in case of using the column of Macherey & Nagel.

Example 4

The 5 serum probes used in example 3 were also used to compare the performance of the inventive device with the performance of two commercial precipitation kits for DNA isolation or purification, the "RTP® DNA/RNA Virus Supersense" kit of Invitek GmbH, Berlin, Germany (Cat-No. 10404002, Lot OC030036) and the "QIAmp® UltraSens™" kit from Qiagen GmbH, Hilden, Germany (Cat-No. 53704, Lot 11862713). Both kits were used according to the protocols of the manufactures (Invitek: Vers. TH11/03.2 March 2003; Qiagen: 01/2003), whereas in case of the Qiagen-kit the protocol was adapted from 1 ml to 5 ml volume.

In comparison with the HighPure™ column adapted for large volumes, the Qiagen-kit isolated an average amount of DNA that was reduced by a factor of around 9, whereas the Invitek-kit isolated an average amount of DNA that was reduced even by a factor of around 80.

LIST OF REFERENCES

Ausubel, F. M., et al., Current Protocols in Molecular Biology, John Wiley & Sons, 1987, 2.1.1-2.4.5

DE 19512361
DE-A-19512369
DE 202 18 503 U1
DE 298 03 712 U1
EP 588564
EP 616638
EP 738733
EP 897978
EP-B-389063
Miller, S. A., et al., Nucleic Acids Res. 16 (1988) 1215
Sambrook, J., et al., Molecular Cloning, Cold Spring Harbor Laboratory Press, 1989, $2^{nd}$ edition, 9.16-9.23
U.S. Pat. No. 4,270,921
U.S. Pat. No. 4,956,298
U.S. Pat. No. 5,104,533
U.S. Pat. No. 5,234,809
U.S. Pat. No. 6,177,009
Vogelstein, B., et al., Proc. Natl. Acad. Sci. USA 76 (1979) 615-619
WO 93/11221
WO 95/14708
WO 96/41810
WO 98/32877
WO 02/053256

What is claimed is:

1. A device for purifying or isolating nucleic acids comprising:
a first hollow body with an inlet opening for receiving a sample and an outlet opening,
a second hollow body with an inlet opening and a surface comprising an outlet opening, wherein the inlet opening of the second hollow body is functionally connected to the outlet opening of the first hollow body, the first hollow body and the second hollow body can be detached from one another, a nucleic acid-binding material is located inside the second hollow body on top of and in contact with the surface and above the outlet opening of the second hollow body, the second hollow body has a volume of between 1 ml and 2 ml and is configured to house the nucleic acid-binding material and position the sample above the nucleic acid-binding material, and the first hollow body has a volume more than 5 ml,
a receiving vessel for receiving the second hollow body while the inlet opening of the second hollow body is functionally connected to the outlet opening of the first hollow body, and
means for applying an underpressure to the outlet opening of the second hollow body, wherein said means for applying an underpressure is connected to a wall of said receiving vessels.

2. The device as claimed in claim 1, wherein the device at least partially fits into a closable vessel.

3. The device as claimed in claim 1, wherein the first hollow body and the second hollow body are connected together by pressing forces.

4. The device as claimed in claim 1, wherein the nucleic acid-binding material comprises silicon dioxide.

5. The device as claimed in claim 4, wherein the silicon dioxide is in the form of fibres or particles.

6. The device as claimed in claim 1, wherein the first and second hollow body together have a volume between 5 and 50 ml.

7. The device as claimed in claim 1, wherein the first hollow body and the second hollow body are connected together by a screwed joint.

8. The device as claimed in claim 1, wherein the first hollow body and/or the second hollow body are/is cylinders or cylinder.

9. The device as claimed in claim 8, wherein the first hollow body comprises a section that becomes conically narrower towards the outlet opening of the first hollow body.

10. The device as claimed in claim 1, wherein the openings/opening of the first hollow body and/or the second hollow body are/is round.

11. The device as claimed in claim 1, wherein the receiving vessel is closable.

12. The device as claimed in claim 1, wherein the nucleic acid-binding material is selected from the group consisting of glass fleece, silica gel and zeolite.

13. The device as claimed in claim 1, wherein the first hollow body or the second hollow body or the receiving vessel for receiving the second hollow body comprises plastic, metal or a composite material.

14. The device as claimed in claim 1, wherein the second hollow body comprises polypropylene.

15. A kit for purifying or isolating nucleic acids from a sample comprising the device of claim 1.

16. The kit as claimed in claim 15 further comprising a chaotropic reagent.

* * * * *